United States Patent [19]

Sanfeliu et al.

[11] Patent Number: 4,965,365

[45] Date of Patent: Oct. 23, 1990

[54] IMIDAZOLE DERIVATIVES AND A PROCESS FOR THE PREPARATION THEREOF

[75] Inventors: Amparo S. Sanfeliu; Lucîa S. Tuero; Maria J. Delgado de Molina González, all of Valencia; Antonio B. Vinas, Barcelona, all of Spain

[73] Assignee: Laboratorios Vinas, S.A., Barcelona, Spain

[21] Appl. No.: 356,013

[22] Filed: May 23, 1989

[30] Foreign Application Priority Data

May 26, 1988 [ES] Spain .................................. 8801655

[51] Int. Cl.$^5$ .............................................. C07F 3/06
[52] U.S. Cl. ...................................... 548/109; 548/342
[58] Field of Search ................. 548/109, 342; 514/400, 514/338

[56] References Cited

U.S. PATENT DOCUMENTS 4,381,395  4/1983  Terajii et al. ........................ 548/342
4,413,129  11/1983  Ochikuga et al. ................... 548/342

Primary Examiner—Mukund J. Shah
Assistant Examiner—D. P. Carr
Attorney, Agent, or Firm—Dressler, Goldsmith, Shore, Sutker & Milnamow, Ltd.

[57] ABSTRACT

Imidazole derivatives and a process for the preparation thereof.

The imidazole derivatives have remarkable antiulcer properties and are of the following formula:

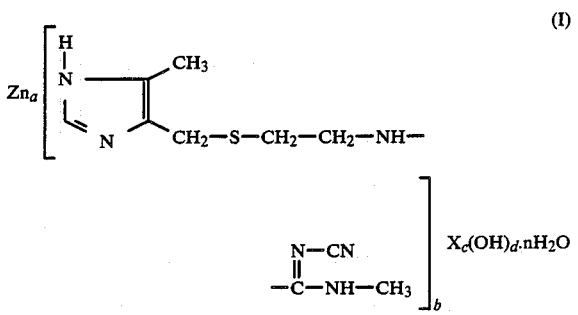

(I)

where X is an anion of pharmaceutically acceptable acids; a is 1, 2, 3, 4 or 5; b is 1, 2, 3, 4, 5, 6 or 7; c is 1, 2, 3 or 4; d is twice a minus c; and n is 0, 1, 2 or 3.

The process for the preparation thereof is based on reacting cimetidine and a zinc compound containing the anion X.

11 Claims, No Drawings

IMIDAZOLE DERIVATIVES AND A PROCESS FOR THE PREPARATION THEREOF

BACKGROUND OF THE INVENTION

1. Field of the Invention

The invention relates to a process for the preparation of imidazole derivatives having the general formula I:

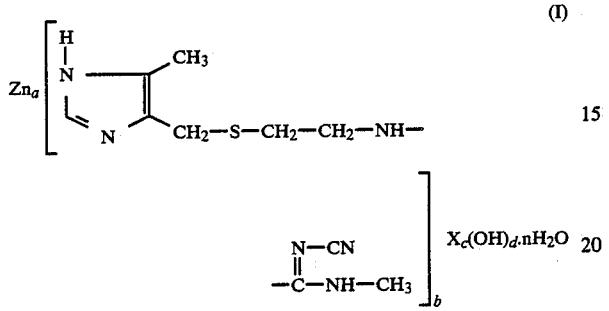

where X is an anion of pharmaceutically acceptable acids, a is 1, 2, 3, 4 or 5; b is 1, 2, 3, 4, 5, 6 or 7; c is 1, 2, 3 or 4; d is twice a minus c; and n is 0, 1, 2 or 3.

The invention also relates to the derivatives of formula I, which have antiulcer properties.

2. Reference to the Prior Art

Chronic gastric and doudenal ulcers are frequent diseases for which there exists a variety of treatments, including dietetic measures, treatment with drugs and surgery. Among these, special attention has been paid in recent years to treatment with secretion inhibitors, one of the most widely used secretion inhibitors around the world being cimetidine of formula II.

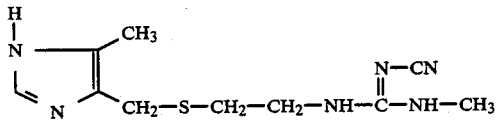

SUMMARY OF THE INVENTION

The imidazole derivatives of the invention provide advantages on improving the antiulcer properties of cimetidine.

In the imidazole derivatives of formula I, X may be an anion of pharmaceutically acceptable inorganic acids such as hydrochloric acid, sulphuric acid, phosphoric acid, hydrobromic acid, hydroiodic acid, hydrofluoric acid and others; or an anion of non-toxic organic acids such as mono- and dicarboxylic aliphatic acids, phenyl substituted alkanoic acids, hydroxyalkanoic acids, alkanedioic acids, aromatic acids, aromatic and aliphatic sulphonic acids and others.

Therefore, X may be chloride, bromide, iodide, fluoride, sulphate, phosphate, chlorate, nitrate, sulphamate, maleate, fumarate, succinate, oxalate, acetate, acexamate, tartrate, citrate, camphorsulphonate, mandelate, butine-1,4-dioate, benzoate, chlorobenzoate, methylbenzoate, hydroxybenzoate, methoxybenzoate, benzenesulphonate, toluenesulphonate, phenylacetate, salicylate, beta-hydroxybutyrate, glycolate, methanesulphonate and the like.

The process of the invention is characterised in that cimetidine is reacted with an X anion containing zinc compound.

Preferably said zinc compound is an organic or inorganic zinc salt and the reaction is carried out in a polar organic solvent such as dimethylformamide, dimethylsulphoxide, acetone, low molecular weight alcohols, etc, or in an organicoaqueous mixture. An alcohol will preferably be used. The reaction temperature may reach the boiling point of the solvent, preferably from room temperature to 60° C. Depending on the type of compound it is wanted to isolate, an alkali or alkaline earth hydroxide may be added or not at the end to alkaline pH, preferably to pH 8. Water may also be added or not, when the reaction has been carried out in an organic solvent alone.

The compounds are prepared in solid form or in the form of a thick oil which, after removal of the solvent under vacuum, becomes a solid.

The formula I compounds have exhibited a potent antiulcer activity. Thus the inhibition of histamine induced gastric secretion "in vivo" in the rat after administration of these Zn-cimetidine compounds i.p. at dose levels of 5 to 50 mg/kg, reaches pH recovery levels of 75%. The antiulcer activity in the rat against ethanol induced ulcers has proved to be satisfactory at dose levels of 100 to 400 mg/kg, p.o., a total ulcer inhibition having been observed in certain cases.

To facilitate the explanation, the invention is illustrated, but not limited, by the following examples:

EXAMPLE 1

Preparation of $Zn_4(cimetidine)_6Cl_3(OH)_5$

A solution of 0.72 g of zinc chloride in 18 ml of water was added dropwise with stirring over a solution of 4.0 g of cimetidine in 130 ml of ethanol. The mixture was stirred for 10 min and 1N sodium hydroxide was added slowly to pH 8. The white precipitate formed was filtered off, washed with ethanol and dried under vacuum at 60° C.

Elementary analysis for $C_{60}H_{101}Cl_3N_{36}O_5S_6Zn_4$ Calculated: C 36.64; H 5.18; Cl 5.41; N 25.64; O 4.07; S 9.78 and Zn 13.30. Found: C 37.11; H 4.87; Cl 5.43; N 26.00; S 10.12 and Zn 13.68.

IR(KBr): 3160, 2970, 2210, 2170, 1590, 1490 and 1110 $cm^{-1}$.

HPLC purity ($\mu$-bondpack C-18; buffer $H_3PO_4$ (pH 2.3)/acetonitrile: 90/10; 1.1 ml/min.; lambda=228 nm): 98.5%.

UV ($H_2SO_4$ 0.1N): lambda max 219±2 nm A (1%, 1 cm): 631.

MS(FAB), m/z: 253, 275, 505, 527, 603, 605, 607 and 757.

EXAMPLE 2

Preparation of $Zn_3(cimetidine)_4(CH_3COO)_2(OH)_4$ 1.16 g of zinc acetate dihydrate, dissolved in 15 ml of water, were added with stirring over a solution of 4.0 g of cimetidine in 80 ml of methanol at 60° C. After 5 minutes stirring, 1N sodium hydroxide was added to pH 8.1. The precipitate obtained was filtered, washed with methanol and dried under vacuum in a muffle at 60° C.

Elementary analysis for $C_{44}H_{74}N_{24}O_8S_4Zn_3$: Calculated: C 37.98; H 5.36; N 24.16; O 9.20; S 9.22 and Zn 14.09. Found: C 38.45; H 5.37; N 24.55; S 9.50 and Zn 14.15.

IR(KBr): 3412, 2922, 2211, 2169, 1586, 1484 and 1103 cm$^{-1}$.

HPLC purity (under the same conditions as in Example 1): 101.2%.

UV (H$_2$SO$_4$ 0.1N): lambda max 218±2 nm A (1%, 1 cm): 587.

MS(FAB), m/z: 253, 275 and 375.

EXAMPLE 3

Preparation of Zn(cimetidine)Cl$_2$ 5.0 g of cimetidine dissolved in 70 ml of ethanol were added slowly over a solution of 2.7 g of zinc chloride in 30 ml of ethanol. The oil formed and the ethanol were separated by decantation. A further 40 ml of ethanol were added, stirring was continued for 15 minutes and the products were separated again by decantation. The oil thus obtained was dried under vacuum at 70° C., was ground and dried again.

Elementary analysis for C$_{10}$H$_{16}$Cl$_2$N$_6$SZn: Calculated: C 30.91; H 4.15; Cl 18.25; N 21.62; S 8.25 and Zn 16.82. Found: C 31.17; H 3.95; Cl 17.88; N 21.80; S 8.20 and Zn 16.62.

IR(KBr): 3628, 3411, 2923, 2208, 1616, 1507, 1437, 1227 and 1087 cm$^{-1}$.

$^1$H NMR (CD$_3$SOCD$_3$, TMS as internal standard). delta: 2.20 (s, 3H); 2.68 (d, 3H); 3.1-3.5 (multiplet, 5H); 3.81 (s, 2H); 6.9-7.1 (multiplet, 2H) and 7.91 (s, 1H).

HPLC purity (under the same conditions as in Example 1): 98.7%.

UV (H$_2$SO$_4$ 0.1N): lambda max 218±2 nm A (1%, 1 cm): 517.

MS(FAB), m/z: 253 and 275.

Experiments are described below to show the therapeutical activity of the compound obtained according to Example 3.

Antiulcer Activity

The antiulcer activity of Zn(cemetidine)Cl$_2$ has been studied in different experimental models, some of which are described below:

(A) histamine induced gastric acid secretion model "in vivo" in the rat.

This activity was measured in Wistar rats of 240±20 g body weight. An endovenous perfusion of a histamine solution stimulated the gastric acid secretion, causing a drop in the intragastric pH. Thereafter, this compound was administered i.p. and the increase in gastric pH caused was evaluated.

At the same time when a group of control animals was administered physiological serum, instead of a compound of the present invention, no significant pH recovery was observed. The results are illustrated in the following table:

| Compound | | pH Recovery (%) |
|---|---|---|
| Zn$_4$(cimetidine)$_6$Cl$_3$(OH)$_5$ | (15 mg/kg) | 56.5 |
| Zn$_3$(cimetidine)$_4$(CH$_3$COO)$_2$(OH)$_4$ | (100 mg/kg) | 55.6 |
| Zn(cimetidine)Cl$_2$ | (15 mg/kg) | 65.5 |
| Control | | ±2.4 |

Thus, at a dose level of 15 mg/kg, a 65.5% pH recovery was obtained.

(B) Necrotic agent model.

The activity of this compound vs cimetidine at equimolecular doses and a control group administered a vehicle was tested using the necrotic agent model, in this case ethanol, described by A. Robert et al. (Gastroenterology, 77: 433, 1979).

The following table summarises the lesion indices (in mm of ulcer) of the three groups studied, as well as the % inhibition of ulcers in the treated groups vs the control (means values±standard error of the mean).

| | mm damaged | % inhibition |
|---|---|---|
| Control | 91.4 ± 8.1 | — |
| Cimetidine | 63.7 ± 7.7$^a$ | 30.3 | t test: a, p< 0.05 vs control; b, p< 0.001 vs control and c, p< 0.001 vs cimetidine.

As may be seen, the synthetised product has an antiulcer activity far superior to that of cimetidine.

What we claim is:

1. An imidazole derivative corresponding to a compound of formula I, $$Zn_a \left[ \begin{array}{c} H \\ | \\ N \\ \diagup \diagdown \\ N \end{array} \begin{array}{c} CH_3 \\ | \\ CH_2-S-CH_2-CH_2-NH- \\ \\ N-CN \\ \| \\ -C-NH-CH_3 \end{array} \right]_b X_c(OH)_d \cdot nH_2O \quad (I)$$

where
  X is an anion selected from the group consisting of chloride and acetate; a is 1, 2, 3, 4 or 5;
  b is 1, 2, 3, 4, 5, 6 or 7; c is 1, 2, 3 or 4;
  d is equal to (2a-c) and n is 0, 1, 2 or 3.

2. The derivatives of claim 1, characterised in that X is the chloride anion, a=4, b=6, c=3, d=5 and n=0.

3. The derivatives of claim 1, characterised in that X is the acetate anion, a=3, b=4, c=2, d=4 and n=0.

4. The derivatives of claim 1, characterised in that X is the chloride anion, a=b=1, c=2, d=n=0.

5. A process for the preparation of imidazole derivatives having the general formula I:

$$Zn_a \left[ \begin{array}{c} H \\ | \\ N \\ \diagup \diagdown \\ N \end{array} \begin{array}{c} CH_3 \\ | \\ CH_2-S-CH_2-CH_2-NH- \\ \\ N-CN \\ \| \\ -C-NH-CH_3 \end{array} \right]_b X_c(OH)_d \cdot nH_2O \quad (I)$$

where X is an anion of pharmaceutically acceptable acids, a is 1, 2, 3, 4 or 5; b is 1, 2, 3, 4, 5, 6 or 7; c is 1, 2, 3 or 4; d is twice a minus c; and n is 0, 1, 2 or 3, characterised in that cimetidine is reacted with a zinc compound containing the X anion.

6. The process of claim 5, characterised in that said compound is a zinc salt containing the X anion.

7. The process of claim 5, characterised in that the X anion is selected from the group formed by chloride, bromide, iodide, fluoride, sulphate, phosphate, chlorate, nitrate, sulphamate, maleate, fumarate, succinate, oxalate, acetate, acexamate, tartrate, citrate, camphorsulphonate, mandelate, butine-1,4-dioate, benzoate, chlorobenzoate, methylbenzoate, hydroxybenzoate, methoxybenzoate, benzenesulphonate, toluenesulphonate, phenylacetate, salicylate, beta-hydroxybutyrate, glycolate and methanesulphonate.

8. The process of claim 5, characterised in that said compound is zinc chloride.

9. The process of claim 5, characterised in that said compound is zinc acetate dihydrate.

10. The process of claim 5, characterised in that the reaction is carried out in a polar solvent.

11. The process of claim 10, characterised in that said solvent is a low molecular weight alcohol, dimethylformamide, dimethylsulphoxide, acetone or aqueous mixtures of the said solvents.

* * * * *